(12) United States Patent
Lenferink et al.

(10) Patent No.: US 6,423,197 B1
(45) Date of Patent: Jul. 23, 2002

(54) SENSOR HOUSING

(75) Inventors: Joris Robert Jan Lenferink, Arnhem; Adelbert Hermanus Tesson, Echtenergrug, both of (NL)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 09/594,312

(22) Filed: Jun. 15, 2000

(30) Foreign Application Priority Data

Jun. 23, 1999 (NL) .............................................. 1012421

(51) Int. Cl.[7] .............................................. G01N 27/30
(52) U.S. Cl. ........................................ 204/408; 204/435
(58) Field of Search ................................ 204/435, 420, 204/415, 408

(56) References Cited

U.S. PATENT DOCUMENTS

| | | | | |
|---|---|---|---|---|
| 2,595,042 A | * | 4/1952 | Wyllie | |
| 3,518,179 A | * | 6/1970 | Bleak et al. | |
| 3,709,796 A | * | 1/1973 | King et al. | |
| 3,833,495 A | * | 9/1974 | Grubb | |
| 4,002,547 A | * | 1/1977 | Neti et al. | |
| 4,012,308 A | * | 3/1977 | Jerrold-Jones et al. | |
| 4,128,468 A | * | 12/1978 | Bukamier | |
| 4,406,766 A | * | 9/1983 | MacDonald | |
| 4,414,093 A | * | 11/1983 | Redey et al. | |
| 4,659,451 A | * | 4/1987 | Fujita et al. | |
| 4,818,366 A | * | 4/1989 | Yonco et al. | |
| 5,490,916 A | * | 2/1996 | Hall | |

* cited by examiner

*Primary Examiner*—T. Tung

(57) ABSTRACT

A sensor housing for accommodating at least one electrode which can be brought into contact with a process fluid, the sensor housing being sealable by means of a porous seal by which an inner chamber is formed between an inner surface of the sensor housing, the external surface of the at least one electrode and the surface of the porous seal, with the inner chamber being filled with a first electrolyte, wherein the sensor housing further comprises a deformable section which enables the inner chamber volume to be variable. The sensor housing may be used in a sensor which is temperature and pressure resistant over a wide range of values.

14 Claims, 2 Drawing Sheets

Fig 1
Fig 2
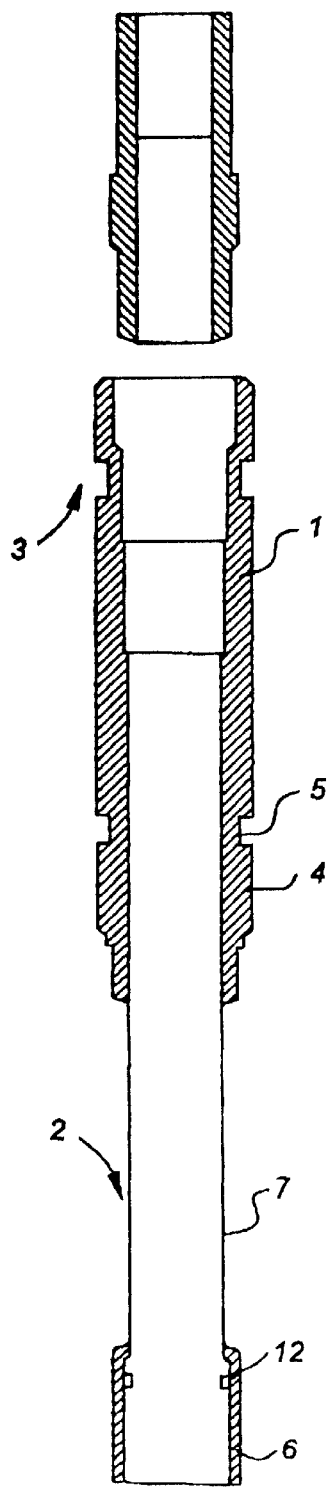
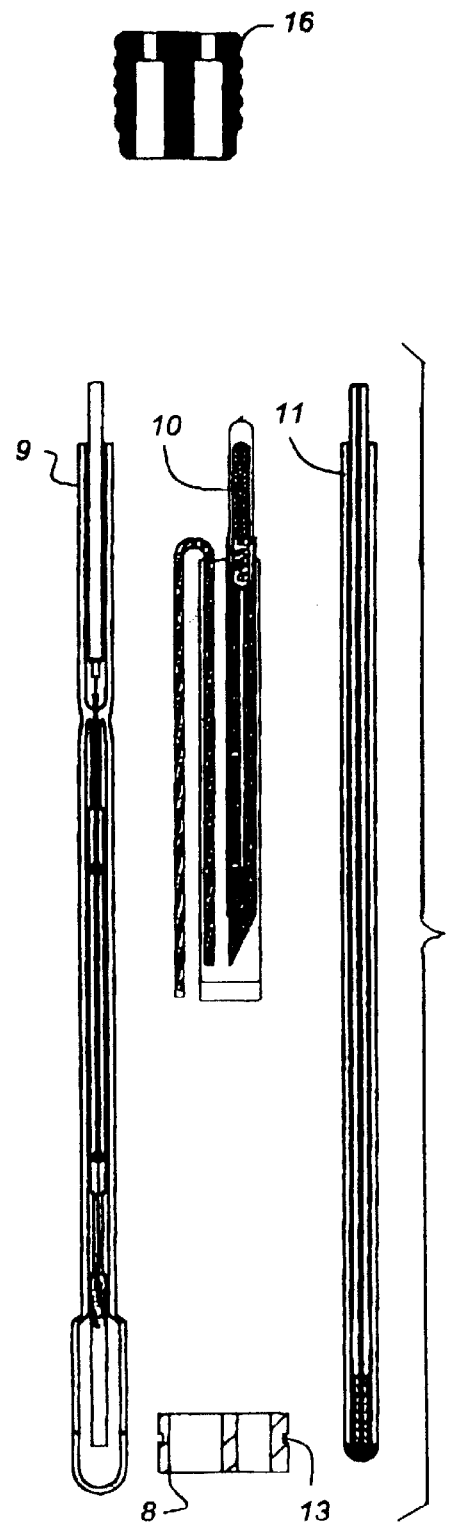

SENSOR HOUSING

BACKGROUND OF THE INVENTION

1. Field of Invention

This invention relates to a sensor used, for example, to sense a process fluid; and more particularly, to a sensor housing used therein.

2. Description of the Prior Art

A conventional sensor housing is disclosed, for example, in U.S. Pat. No. 4,128,468 which describes an ion sensitive electrode structure which can be used, for example, to measure the pH of a process fluid. This structure comprises an elongated tubular housing which holds a glass electrode and a reference electrode therein. The elongated housing is sealed toward one end by means of a sealing annulus through which signal wires of the electrodes are passed. The other end of the housing is brought into contact with the process fluid to be measured. This end of the housing is sealed by a plug of porous material, for example, porous polytetrafluoroethene (PTFE). Through the porous plug, the reference electrode is in electrochemical contact with the process fluid. Located in the plug is a passage into which the glass electrode is disposed, with the result that the sensitive end of the glass electrode is projected outwards at the process end of the housing.

The process industry generally makes use of a thickened electrolyte in the pH sensor to prevent unduly rapid loss of the electrolyte, particularly when a relatively highly porous material is used for the plug which serves as the liquid junction. Because of the relative size (about 10 microns) of the porous PTFE material of the plug, unduly rapid loss of electrolyte can occur if the electrolyte is not sufficiently viscous, thereby significantly limiting the service life of the pH sensor. The thickened electrolyte has a drawback, however, namely, that its volume increases relatively markedly with increase of temperature. The volume can increase by the order of magnitude of from 5% to 10%. If the walls of the housing which hold the thickened electrolyte are stiff, and if the temperature coefficient of the material of the housing is such that the increase in volume of the housing is less than that of the electrolyte, considerable pressure will build up in the sensor. This may lead to rupture of the housing, to the plug being pushed away, or to loss of electrolyte. In the first two cases, electrolyte would disappear from the sensor and the sensor will become useless. In the third case, a decrease in temperature will result in the ingress of the process fluid to make for loss of electrolyte, thereby contaminating the electrolyte. This would lead to uncalibrated operation of the pH sensor and Consequent unreliable reading.

U.S. Pat. No. 4,659,451 discloses a reference electrode for measuring fluid under high pressure. The reference electrode can form part of a pH measuring circuit and is provided with an internal liquid containing space therein and a liquid junction, one end of which is exposed to the process fluid and the other end of which is exposed to the liquid contained in the liquid containing space. Flexible bellows are provided between the spaces in contact with the internal liquid containing body to compensate for the pressure, of the high pressure liquid, which is exerted on the internal liquid through the liquid junction. All of these components are acccommodated in a sensor housing which is rigid.

The flexible bellows are designed to transmit the pressure of the process fluid to the inside of the reference electrode. To this end, the pressure of the process fluid needs to be transmitted through a capillary to the flexible bellows. The capillary can easily become clogged by the process fluid resulting in the pressure being partially or entirely blocked from transmission. Moreover, in this sensor, various junctions are present where various parts of the sensor are fastened to one another. For example, the flexible bellows are fastened to the glass reference electrode by fastening means. However, disadvantageously, the fasteners inherently form the weak point of the sensor.

U.S. Pat. No. 4,406,766 discloses a pH sensor for measuring the pH of a process fluid under elevated temperature and pressure, wherein the sensitive parts of the measuring electrodes are not exposed to the high temperatures and where no contamination of internal electrolyte occurs upon pressure changes in the process fluid. This is achieved by the sensitive parts of the measuring sensors being arranged at a distance from the end of the pH sensor which comes into contact with the process fluid. Attachment of the pH sensor to a vessel or like containing process fluid, is effected by means of a number of thermal barriers, so that the sensitive parts of the pH sensor remain at roughly ambient temperature. Attached to the ends of the glass electrode and reference electrode, which are at a distance from the end of the pH sensor in contact with the process fluid, are deformable wall bodies contained in a chamber. The pressure of the process fluid can be transmitted through a capillary to the chamber. The pressure of the process fluid is thereby transmitted at the same time through the deformable wall bodies to the electrolyte present at the glass electrode and reference electrode. Hence, the internal pressure of the glass electrode and the reference electrode is equal to the pressure in the process fluid.

However, this known pH sensor has a number of problems. First, the deformable wall bodies are made of a material which is different from that of the glass electrode and the reference electrode, which means that the junction is inherently weak. Also, the pH sensor is provided with a capillary for transmitting the pressure. This capillary can easily become clogged, thereby resulting in partial or complete loss of pressure compensation, which in turn results in fracture or leakage of the electrolyte.

Thus, the conventional sensors all have various disadvantages and deficiencies.

SUMMARY OF THE INVENTION

Accordingly, an object of the invention is to overcome the aforementioned and other deficiencies and disadvantages of the prior art.

Another object is to provide a sensor housing, such as for example for use in a pH sensor, which is temperature resistant and pressure proof. That is to say, with the invention, over an entire specified pressure and temperature range of the sensor, no process fluid will be able to penetrate the sensor even when the pressure and temperature variations would otherwise cause contamination of the electrolyte.

The foregoing and other objects are attained by the invention, which in one aspect comprises a sensor housing for accommodating at least one electrode which contacts a process fluid through a porous opening of an inner chamber formed between an inner surface of the sensor housing and an external surface of the at least one electrode with the inner chamber being filled with electrolyte, wherein one or more deformable sections are provided to enable the space of the inner chamber to be variable, that is to allow the space to increase or decrease in volume.

An advantage of the invention sensor using the invention housing is that any expansion, caused by a higher temperature of the process fluid, or of the thickened electrolyte is absorbed by the one or more deformable sections of the sensor housing. As a result of out-ward deformation of the at least one deformable section, the internal volume of the space of the sensor increases, and no pressure build up within the housing occurs. Thus, no leakage of electrolyte will take place upon subsequent cooling of the sensor with the otherwise possible contamination of the electrolyte.

In a preferred embodiment, the sensor housing and deformable sections are made of one material. This allows for simple fabrication of the sensor housing. Also, there is absence of junctions between different materials which prevents occurrence of fractures and leaks in the housing.

In a further embodiment, the material of the sensor housing, with the exception of the deformable sections, has a second material added thereto. The second material can be a stiffening material which will provide a stiffer and more robust sensor housing, while the deformable sections remain sufficiently flexible to provide a variable internal space.

In a further embodiment, the housing and deformable sections are made of one piece construction. Thus, there is no junction between parts of the sensor housing and hence the sensor housing has no inherent weakness and is more resistant to external influences.

In a still further embodiment, the at least one deformable section or sections are located on that part of the housing which is contactable with the process fluid. This allows the pressure of the process fluid to be transmitted through the deformable sections to the internal space of the housing. As a result, no pressure differentials will occur between the inner chamber and the process fluid. This avoids use of a capillary means, hence, the invention is not vulnerable to blockage.

Preferably, in another embodiment of the sensor housing, the housing is provided with one or more bracing ribs at the locations of the deformable sections. As a result, the sensor housing is more rigid, which means that the housing can be attached more readily and with no risk of damage to the interior thereof, for example, in a process vessel. Furthermore, this also results in better protection of the electrodes placed within the housing, for example, a glass electrode and a reference electrode which generally comprises rigid glass parts.

In another embodiment, the material of the sensor housing is resistant to chemicals. For example, the material may be a plastic, such as PVDF, which offers good resistance up to pH values of 12 and above, depending on the temperature.

In a further embodiment, the one or more deformable sections are formed by local attenuations of walls of the sensor housing. Preferably, the deformable sections have a maximum thickness of 0.50 mm, for example, a thickness of 0.25 mm. This provides sufficient deformability of the sensor housing to absorb variations in the space of the inner chamber. Advantageously, it is possible to use standard fabrication techniques to fabricate the sensor housing of the above discussed thicknesses.

A second aspect of the invention encompasses a sensor comprising a sensor housing of the invention. One embodiment relates to a pH sensor comprising a reference electrode which is located in the inner chamber of the sensor housing.

In a further embodiment, the sensor further comprises a glass electrode to measure the pH of a process fluid. A porous seal is provide with a passage into which the glass electrode is fitted.

A yet further embodiment relates to a sensor which is additionally provided with a temperature sensor disposed in the sensor housing.

A still further embodiment of the sensor is an additionally provided ORP electrode or liquid earth electrode which is disposed in the sensor housing and having a contact projected through the porous seal to contact the process fluid. The liquid earth electrode can also be used for diagnostic purposes relating to action of the sensor during operation.

A third aspect of the invention relates to a method of fabricating the sensor housing of the invention. For example, the sensor housing can be fabricated using an injection moulding process or alternatively a vacuum forming process.

The one or more deformable sections of the sensor housing can be fabricated integrally, or alternatively, the one or more deformable sections can be fabricated by partial removal of the material thereof. An alternative fabrication technique is to apply the one or more deformable in a further procedural step using welding process. As a result, a sensor housing is obtained of one piece construction with a section being deformable so that an inner chamber having a space or volume which is variable, that is space that can be increased or decreased, is obtained. The one or more deformable sections can be obtained also by use of a glued joint.

BRIEF DESCRIPTION OF THE DRAWINGS

FIG. 1 is a cross sectional view depicting a preferred illustrative embodiment of the invention.

FIG. 2 are cross sections depicting various elements disposed within the sensor housing, for example, to form a pH sensor.

DETAILED DESCRIPTION OF THE PREFERRED EMBODIMENTS

Figure 3:
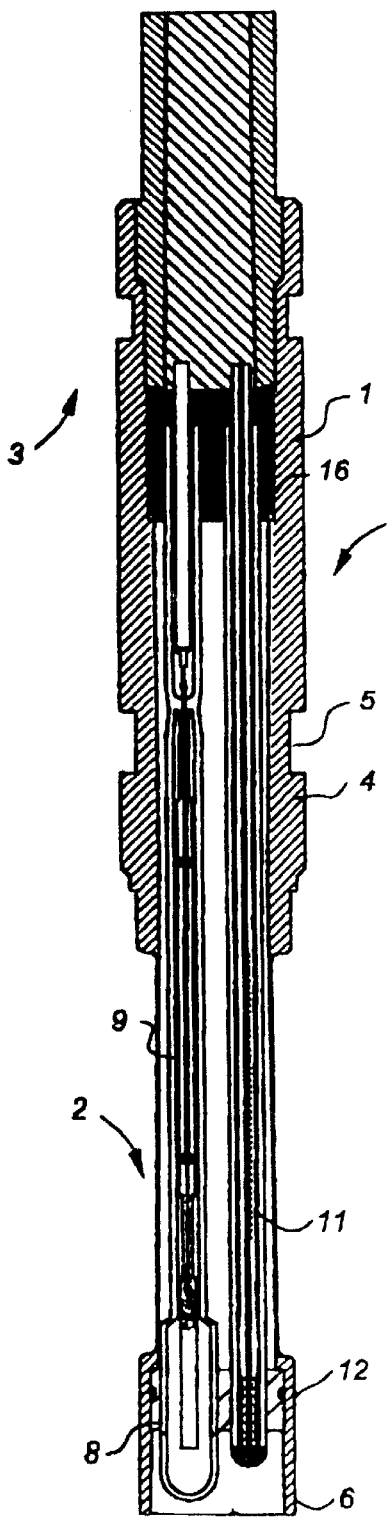
FIG. 3 is a cross sectional view depicting a pH sensor provided with a sensor housing of the invention.

FIG. 1 shows a sensor housing 1 which is preferably of an elongated tubular shape, comprising a process end 2 and a connection end 3. The sensor housing 1 can be fastened by means of a non-tapering screw thread 4, in an opening of, for example, a process vessel not shown. The sensor housing 1 is further provided with a groove 5, into which an O-ring can be fitted to connect housing 1 to the process vessel in a fluid tight manner. At the process end 2, the sensor housing 1 is provided with a protective collar 6 which serves to protect the electrode sections which project out from the sensor g housing 1. The section of the sensor housing 1 between the screw thread 4 and the protective collar 6 is provided with deformable sections 7 which enable the space within the sensor housing 1 to vary, that is to increase or decrease. The upper part (not labelled) is shown separated from the top part of the housing 1, but, as shown in FIG. 3, the upper part is fit into the top part of the housing 1 in an operative condition.

FIG. 2 shows cross sections of various elements which are fitted within or to the sensor housing 1 to form, for example, a pH sensor 15. These components are shown more clearly in FIG. 3 fitted within and to the sensor housing 1. A porous seal can, for example, be fitted on the inside of the protective collar 6 to form a liquid junction between the process fluid and an electrolyte contained in the inner chamber of the housing 1. The porous seal 8 has an O-ring groove which forms a fluid tight seal with the O-ring in place. In an embodiment of the sensor housing 1, the protective collar 6 is provided on the inside with a rim 12 (see FIG. 1) which at the top of porous seal 8 is able to engage, for example, a groove 13, as a result of which the porous seal 8 can be readily fastened in the sensor housing 1 so as to provide a suitable seal.

Also, a glass electrode 9 can be disposed in housing 1 (as shown in FIG. 3) whose membrane glass projects through an opening in the porous seal to contact the process fluid. The glass electrode 9 can, for example, be a glass electrode having a silver/silver chloride collector pin in a pH buffered KCl solution, as known to those skilled in the art. To form a combined pH electrode 15, the sensor housing 1 should further comprise a separate reference electrode 10 or alternatively at least a reference collector pin of, for example silver/silver chloride in a KCl solution which is present in the sensor housing 1, as known to those skilled in the art. The reference electrode 10, in the embodiment shown in FIG. 2, need not be in direct contact with the process fluid. As shown, the reference electrode 10 is placed in a salt bridge which is formed by sensor housing 1. The electrochemical connection in this case runs from the process fluid through the liquid junction 8, the electrolyte present in the sensor housing 1, the second liquid junction in the reference electrode 10 and the electrolyte in the reference electrode to the collector point or pin of the reference electrode. In addition, the pH sensor 15 can further comprise a temperature sensor combined with a liquid earth electrode 11, the latter of which, like the glass electrode 9, contacts the process fluid through an opening in the porous seal 8. The temperature sensor 11 measures the temperature of the process fluid, and the liquid earth electrode forms a well defined earth or ground for a stable pH measuring circuit. The liquid earth electrode can also be used for on-line diagnostics concerning the action of the entire pH sensor 15. The various electrodes 9, 10 and 11 are fastened within the sensor housing 1, as shown partially in FIG. 3, with the aid of a sealing plug 16 which is fitted on the connection end 3 of the sensor housing 1 and which seals the internal space of the sensor housing 1.

As described above, the porous seal 8 is provided with one or more openings through which the respective electrodes 9, and 11 disposed in the housing 1 can be projected outward to contact the process fluid. The openings in the porous seal 8 are matched to the electrodes 9 and 11 so as to form a suitable fluid tight seal at the contact surfaces. Alternately, the grooves and matching O-rings can be used to seal the various junctions between electrodes 9, 10 and 11 and the porous seal 8. As a result, diffusion is the only way in which the process fluid can penetrate into the inner chamber and contaminate the electrolye disposed therein, and potentially leading to an incorrect measurement result or a defective pH sensor 15. At the same time, the electrolyte disposed in the housing 1 is prevented from leaking out along the contact faces.

The inner chamber or space defined by the inner wall of the sensor housing 1, the outsides of the various electrodes 9, 10 and 11, the sealing plug 16 and the porous seal 8, is filled with an electrolyte. To prevent the electrolyte from leaking out too rapidly through the porous seal 8, a thickened electrolyte is used. The. thickened electrolyte is generally a thickened, supersaturated KCl solution. Examples of thickeners used include hydroxyethyl cellulose (HEC); polyethylene glycol (PEG); polyvinyl alcohol (PVA) or polyacrylamide (PAA).

FIG. 3 shows a pH sensor 15 provided with a sensor housing 1 wherein the pH sensor 15 comprises the above described electrodes 9, 10 and 11 of which the reference electrode 10 is located behind the glass electrode 9 and temperature and liquid earth electrode 11 and is hence not visible in this cross sectional view of FIG. 3, but which is understood to be so disposed.

The pH sensor 15 comprises a thickened electrolyte so that topping up of the reference electrolyte, and consequently maintenance is reduced in this invention. If the electrolyte is not thickened, it will leak away relatively rapidly, thus shortening the service life of the pH sensor 15. A temperature increase of the process fluid causes an increase in volume of the electrolyte. If the temperature coefficient of the sensor housing material is such that the increase in the internal or inner chamber space is less than that of the electrolyte volume, a significant pressure build up will result within the sensor housing, which may lead to fractures or cracks in the housing 1, and immediately or soon thereafter lead to failure of the pH sensor 15. The high pressure may also force the porous seal 8 out of the housing. This will result in loss of electrolyte. Even if a small amount of electrolyte is lost, however, any subsequent drop in temperature will produce a negative pressure within the sensor housing 1. This may cause the ingress of process fluid into the inner chamber of the housing 1 and hence contamination of the electrolyte, which in turn may lead to a significantly shorter service life of the pH sensor 15.

However, since one or more deformable sections 7 are provided in the invention, the increase in volume caused by an increase in temperature can be readily absorbed by the housing 1. The one or more deformable wall sections are preferably disposed between the screw thread 4 and the protective collar 6. Thus, during operation the deformable section or sections are in contact with the process fluid. The deformable sections 7 will transmit the pressure of the process fluid to the electrolyte, and hence, the pressure on both sides of the porous seal 8 will be equal. Thus, the pH sensor 15, comprising the sensor housing 1 of the invention, is resistant to variations in both temperature and pressure.

Figure 4:
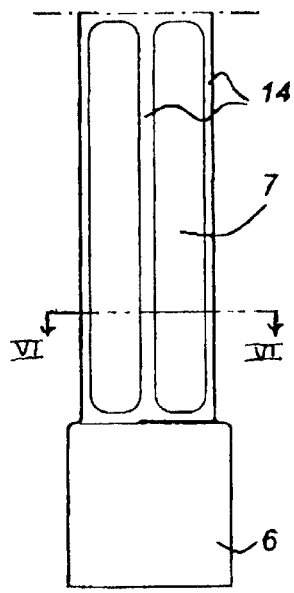
FIG. 4 is a side view depicting part of the sensor housing of the invention.

FIG. 4 shows a side view of part of the sensor housing 1 wherein disposed in the longitudinal direction of the housing 1 are a plurality of bracing ribs 14 disposed on that part of the sensor housing 1 whereat are disposed the one or more deformable sections 7. This results in greater strength of the sensor housing 1. However, the ribs 14 also allows expansion and compression of the inner chamber space caused by the deformable sections 7. As a result, there is greater strength in the sensor housing structure and the risk of damage to the electrodes 9,10 and 11 disposed therein when the sensor is handled and installed, is reduced without reduction in the variability of the space of the inner chamber.

Figure 5:
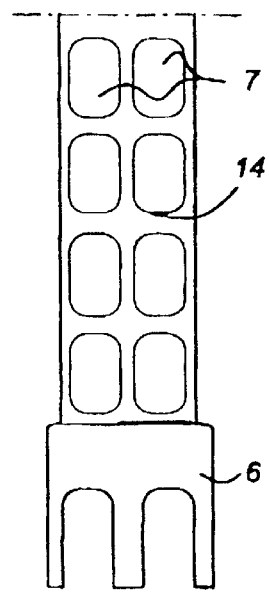
FIG. 5 is a side view depicting part of the sensor housing of the invention.

FIG. 5 shows a side view of part of the sensor housing wherein the one or more deformable sections 7 are surrounded by criss crossing bracing ribs 14. The degree of expansion and compression of the sensor housing 1 is more restricted, but, a suitable effect is achieved by suitable choice of dimensions and thicknesses of the material in the deformable sections. Other combinations of the deformable sections 7 and the bracing ribs 14 are also possible. The protective collar 6 in FIG. 5 takes the form of a number of projecting teeth. This promotes the flow of process fluid around the electrodes, while concurrently affording suitable protection of the electrodes.

Figure 6:
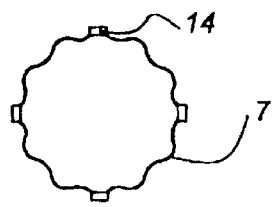
FIG. 6 is a cross sectional view depicting the sensor housing of FIG. 4 taken along sectional line VI—VI.

FIG. 6 shows a cross sectional view of the sensor housing 1 shown in FIG. 4 and along section line VI—VI, to depict the deformable section 7 which is formed by corrugated sections of a thin material, and the bracing ribs 14 formed by thicker sections of the material. The corrugated deformable sections 7 can be corrugated in such a manner that the sensor housing 1 can be fabricated in a simple manner with the aid of moulds, for example, by means of injection moulding or other techniques. It is apparent to those skilled in the art that the deformable sections 7 can also be fashioned in other ways, for example, corrugated sections running perpendicular to the longitudinal direction of the sensor housing 1.

The sensor housing 1 is preferably fabricated from one material, thus avoiding vulnerable junctions between different materials and enabling simple fabrication. In addition, the sensor housing 1 is preferably made of one piece construction, so that junctions are not present in the sensor housing. As a result, the design of the sensor housing 1 is inherently stronger. Also, there is less risk in the invention of leakage, fractures and cracks at the junctions. Preferably, sensor housing 1 is fabricated from a material which is resistant to corrosive action of most common process fluids. As an example of a suitable material having the desired characteristics is the plastic PVDF, which is resistant to chemicals and belongs to the group of fluoropolymers which are resistant to chemicals,etc. At the same time, it is possible with the invention for applications requiring a less extensive range, to fabricate the sensor housing from ,for example, polypropylene or other common plastics. In an alternative embodiment of the sensor housing 1, the material of the housing, with the exception of the deformable sections, has a stiffening material, such as glass, added thereto. The combination of a glass filled material for the sensor housing 1, and a pure material ("virgin material") for the deformable sections 7, result in a rugged, robust sensor housing 1 having the advantages of a variable internal space provided by the deformable sections 7.

Preferably, the sensor housing is fabricated with the aid of an injection molding process. This allows the sensor housing 1 to be fabricated in one piece, the deformable sections 7 having a thickness of at most 0.50 mm, for example 0.25 mm, being formed at the same time. Alternately, the sensor housing 1 can be fabricated with the aid of a vacuum forming process. As noted above, the deformable sections 7 can be formed simultaneously or concurrently with the fabrication of the sensor housing 1 or in the further procedure step, wherein the deformable sections 7 are formed by partial removal of material thereat.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. In a sensor housing having two opposite ends and accommodating at least one electrode which is brought into electrochemical contact with a process fluid through a porous liquid junction located at one end of said sensor housing and adjacent an inner chamber formed between an inner surface of said sensor housing and an external surface of said at least one electrode, with said inner chamber being filled with an electrolyte, the improvement wherein
said sensor housing comprises a non-deformable section and at least one deformable section which enables volume of said inner chamber to be variable to compensate for pressure changes; wherein
said sensor housing including said at least one deformable section is of one material, and wherein
said non-deformable section comprises bracing ribs disposed adjacent said at least one deformable section,
whereby contamination by said process fluid into said sensor housing is prevented over a range of temperatures and pressures.

2. The housing of claim 1, wherein said non-deformable section comprises a stiffening agent.

3. The housing of claim 1, wherein said at least one deformable section and said non-deformable section of said sensor housing are made of one piece construction.

4. The housing of claim 1, wherein said at least one deformable section is disposed to be in contact with said process fluid.

5. The housing of claim 1, wherein said sensor housing comprises a wall, and said at least one deformable section thereof is formed by attenuations in said wall.

6. The housing of claim 1, wherein said one material of said sensor housing is of a chemical resistant material.

7. The housing of claim 6, wherein said chemical resistant material is plastic.

8. The housing of claim 7, wherein said plastic is polyvinyl difluoride.

9. The housing of claim 1, wherein said at least one deformable section has a wall of maximum thickness of 0.50 mm.

10. The housing of claim 9, wherein said wall of said at least one deformable section is of a thickness of 0.25 mm.

11. A sensor comprising:
at least one measuring electrode;
a sensor housing accommodating said at least one measuring electrode in such a manner that said at least one measuring electrode extends through a porous liquid junction to directly contact a process fluid;
an inner chamber formed between an inner surface of said sensor housing and an external surface of said at least one measuring electrode;
an electrolyte filling said inner chamber; and
a reference electrode disposed in said inner chamber; wherein
said sensor housing comprises a non-deformable section and at least one deformable section which enables volume of said inner chamber to be variable to compensate for pressure changes; wherein
said sensor housing including said at least one deformable section is of one material, and wherein
said non-deformable section comprises bracing ribs disposed adjacent said at least one deformable section,
whereby contamination by said process fluid into said sensor housing is prevented over a range of temperatures and pressures.

12. The sensor of claim 11, wherein said at least one measuring electrode comprises a glass electrode for measuring pH of said process fluid.

13. The sensor of claim 11, wherein said at least one measuring electrode comprises a liquid earth electrode.

14. The sensor of claim 11, further comprising a temperature sensor disposed partially in said inner chamber.

* * * * *